United States Patent [19]

Becker

[11] Patent Number: 4,920,264

[45] Date of Patent: Apr. 24, 1990

[54] METHOD FOR PREPARING SAMPLES FOR MASS ANALYSIS BY DESORPTION FROM A FROZEN SOLUTION

[75] Inventor: Christopher H. Becker, Menlo Park, Calif.

[73] Assignee: SRI International, Menlo Park, Calif.

[21] Appl. No.: 298,649

[22] Filed: Jan. 17, 1989

[51] Int. Cl.$^5$ .............................................. H01J 44/04
[52] U.S. Cl. .................... 250/282; 250/288; 436/173
[58] Field of Search ................. 250/282, 288; 436/173

[56] References Cited

U.S. PATENT DOCUMENTS

| | | | |
|---|---|---|---|
| 3,997,298 | 12/1976 | McLafferty et al. | 23/253 R |
| 4,230,946 | 10/1980 | Wells et al. | 250/425 |
| 4,243,887 | 1/1981 | Hillenkamp et al. | 250/423 P |
| 4,259,572 | 3/1981 | Brunnee et al. | 250/281 |
| 4,686,366 | 8/1987 | Stuke | 250/287 |
| 4,733,073 | 3/1988 | Becker et al. | 250/288 |

OTHER PUBLICATIONS

Jonkman et al, Analytical Chemistry, vol. 50, No. 14, Dec. 1978, pp. 2078–2082.
Busch, K. L. et al, "Mass Spectrometry of Large, Fragile, and Involatile Molecules", Science, vol. 218, Oct. 15, 1982, pp. 247–254.
Rinehart, K. L., Jr., "Fast Atom Bombardment Mass Spectrometry", Science, vol. 218, Oct. 15, 1982, pp. 254–260.
Vestal, M. L., "High-Performance Liquid Chromatography-Mass Spectrometry", Science, vol. 226, Oct. 19, 1984, pp. 275–281.
Wong, S. F., et al, "Multiple Charging in Electrospray Ionization of Poly(ethylene glycols)", Journal of Physial Chemistry, vol. 92, 1988, pp. 546–550.

Primary Examiner—Jack I. Berman
Attorney, Agent, or Firm—John P. Taylor

[57] ABSTRACT

A method is disclosed for the processing and preparation of a sample of one or more nonvolatile or thermally labile molecules for mass spectral analysis which comprises providing a solution of such molecules dissolved in a solvent, freezing the solution of dissolved molecules to form a frozen solution, and exposing the frozen solution to a source of energy to desorb the molecules to be analyzed from the surface of the frozen solution. The desorbed molecules may be photoionized after desorption, if necessary, and then conventionally analyzed in a mass spectrometer. The method mitigates or minimizes possible fragmentation or clustering of such large molecules during desorption from the frozen sample as well as providing a more reliable and uniform desorption. If desired the desorbed molecules may be subjected to a separate and controlled fragmentation step prior to entering the final mass spectral anslysis zone. The method may be interfaced with liquid chromatography equipment.

24 Claims, 2 Drawing Sheets

FORMING A SOLUTION OF A LARGE MOLECULAR WEIGHT COMPOUND TO BE ANALYZED BY MASS SPECTRAL ANALYSIS BY DISSOLVING THE LARGE MOLECULES IN A LOW MOLECULAR WEIGHT SOLVENT

↓

FREEZING THE SOLUTION AND COOLING IT DOWN TO A TEMPERATURE WHERE THE VAPOR PRESSURE IS LESS THAN $10^{-5}$ TORR

↓

DESORBING A SURFACE LAYER OF MOLECULES FROM THE FROZEN SOLUTION IN A VACUUM CHAMBER USING A DESORBING ENERGY SOURCE

↓

PHOTOIONIZING THE DESORBED MOLECULES AT AN ENERGY LEVEL WHICH WILL NOT FRAGMENT THE DESORBED MOLECULES

↓

ANALYZING THE DESORBED AND IONIZED MOLECULES IN A MASS SPECTRAL ANALYSIS APPARATUS

FIG. 1

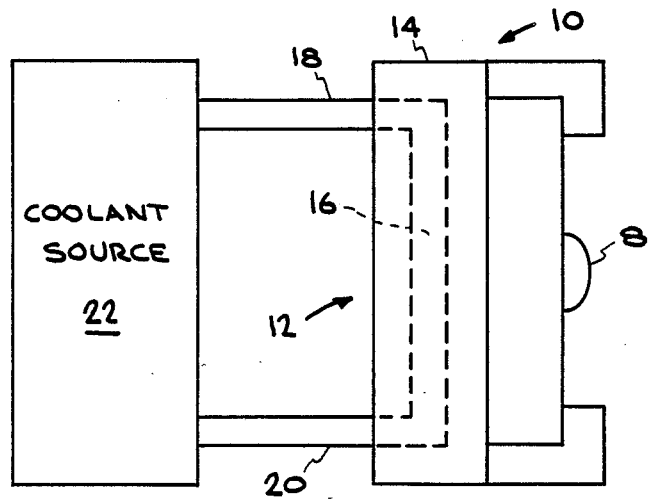

FIG. 3

METHOD FOR PREPARING SAMPLES FOR MASS ANALYSIS BY DESORPTION FROM A FROZEN SOLUTION

BACKGROUND OF THE INVENTION

1. Field of the Invention

This invention relates to the preparation of samples for mass analysis. More particularly, this invention is directed to the preparation of samples of large nonvolatile or thermally labile molecules for mass analysis by freezing a solution of the large molecules, desorbing the frozen molecules, and then, if the desorbed molecules are not already ionized by the desorbing means, ionizing the desorbed molecules prior to introducing the ionized molecules into a mass analysis zone. This method is amenable to mechanical interfacing to liquid chromatography.

2. Description of the Related Art

In the mass analysis of molecules combined with liquid chromatography techniques, a liquid is often vaporized and the molecules in the vapor are ionized prior to introduction into a mass analysis instrument or the solvent is evaporated and the resultant molecules are ionized by desorbing particles or photons for the mass analysis instrument. However, the vaporization or desorption techniques conventionally utilized in preparing samples of large nonvolatile or thermally labile molecules for analysis can result in uncontrolled fragmentation or clustering of such large molecules as well as unsuccessful vaporization or desorption of the solvated molecules (nonreliability).

McLafferty et al U.S. Pat. 3,997,298 describe a liquid chromatography-mass spectrometry apparatus in which a portion (or portions) of the eluted effluent from the column is introduced directly into the ionization chamber of a chemical ionization mass spectrometer with sufficient vacuum pumping.

Brunnee et al U.S. Pat. 4,259,572 describe a method for preparing ionized samples for mass spectral analysis by placing the effluent from a liquid chromatography column on a moving belt conveyor, evaporating the solution medium to leave the substance behind, then moving the belt into the vacuum environment of an ionization chamber associated with a mass spectrometer where it is exposed to highly concentrated energy in the form of ions, electrons, or photons, with the latter coming from a laser. The patentees state that the primary concept common to the various embodiments disclosed requires the exposure of the sample on the conveyor belt always within very short intervals, namely within fractions of seconds, to highly concentrated energy in such a way that by the concentration of energy, the connections between molecules in the sample are locally separated without or prior to any chemical decomposition of the molecules.

Stuke U.S. Pat. 4,686,366 discloses a laser mass spectrometer in which a pulsed laser beam is used to ionize the molecule to be analyzed in the mass spectrometer. The duration of the laser pulse is limited to a few picoseconds to avoid fragmentation of the molecule being analyzed.

While these patents describe methods which purport to avoid undesirable fragmentation of the molecule, in actual practice such techniques are only partially successful, depending upon the particular molecule or molecules being analyzed with some molecules fragmenting in uncontrolled fashion or clustering, and thus such methods are considered to be unpredictable and therefore unreliable.

Becker et al U.S. Pat. 4,733,073, by the inventor and others and assigned to the assignee of this invention, and cross-reference to which is hereby made, teaches a method and apparatus for the spectral analysis of a sample in which a probe beam such as an ion beam, electron beam, or a laser beam, is directed against a surface to be analyzed to cause a sample of material to be removed from the surface. A beam of electromagnetic radiation, such an an untuned high-intensity laser beam, is then directed to a spatial region above the surface causing non-resonant photoionization of the removed surface sample within the beam of radiation. The ionized sample is then subjected to mass spectral analysis.

Over about the last decade, many examples have appeared in the literature describing the mass spectrometry of large nonvolatile or thermally labile molecules by the use of particle or photon bombardment of the sample such as referred to in the patent of Brunnee et al. One article making a review of the development is by K. L. Busch and R. G. Cooks, entitled "Mass Spectrometry of Large, Fragile, and Involatile Molecules", published in Science, Volume 218, (1982) at pages 247–254.

One of the methods described in this article is called fast atom bombardment (FAB). The FAB approach is reviewed in more detail in an article by K. L. Rhinehart, Jr., entitled "Fast Atom Bombardment Mass Spectrometry", published in Science, Volume 218, (1982) at pages 254–260. In the FAB approach, the sample is placed in solution in a liquid of low volatility, commonly glycerol. That solution is then bombarded by atoms of kiloelectron volt energy to directly produce ions for mass analysis. One of the primary potential benefits of the FAB technique is the continual supply of sample molecules to the surface. However, drawbacks include molecular types which avoid segregation to the surface, the accumulation of fragmented molecules at the surface, interferences from the solvent molecules, as well as the resultant difficulty of quantifying relative amounts in mixed samples.

Another mass spectrometric approach involving a solution of the sample involves methods of spraying the solution directly for vaporization and ionization preceding mass analysis. The first of such spraying methods, the so called thermospray technique, is described by M. L. Vestal in an article entitled "High-Performance Liquid Chromatography-Mass Spectrometry", published in Science, Volume 226, (1984) at pages 275–281 and is defined therein as the production of a supersonic jet of vapor with entrained particles or droplets by application of sufficient heat to a capillary to effect controlled partial vaporization of a liquid as it passes through the capillary.

The second spray method, the so called electrospray method, is described by Wong et al in an article entitled "Multiple Charging in Electrospray Ionization of Poly-(ethylene glycols)", published in the Journal of Physical Chemistry, Volume 92 (1988) at pages 546–550, in which the authors describe a method wherein the solution enters the electrospray chamber through a metal hypodermic needle which is maintained at a high voltage relative to a metallized capillary tube at ground potential. The high field at the needle tip charges the surfaces of the emerging liquid dispersing it into a fine spray of charged droplets. As the droplets proceed toward the capillary tube, the solvent evaporates leaving only the charged solute which then proceeds through the capillary tube to the mass spectrometer.

However, in each of the above cases, the preparation of large nonvolatile molecules, such as biomolecules, for mass spectral analysis still incurs the risk of uncharacteristic fragmentation or clustering or otherwise uncharacteristic or unreliable isolation of the large molecule while attempting to vaporize the molecule prior to or during ionization of the molecule.

SUMMARY OF THE INVENTION

It is, therefore, an object of this invention to provide a method of preparing samples of one or more large types of molecules for mass spectral analysis in a manner which will minimize the risk of undesirable fragmentation of the molecules.

It is another object of this invention to provide a method of preparing pure or mixed samples of large molecules for mass spectral analysis in a manner which will minimize the risk of nonspecific fragmentation or providing nondistinct and unreliable identification of the molecules.

It is still another object of this invention to provide a method of preparing samples of one or more large molecules for mass spectral analysis by dissolving the large molecules to be analyzed in a solvent, or using an already existing appropriate solution; then freezing the resultant solution; and then desorbing large molecules from the surface of the frozen solution in a reliable and uniform manner for subsequent ionization while minimizing the risk of fragmentation during the desorption step.

It is yet another object of this invention to provide a method of preparing samples of one or more large molecules for mass spectral analysis by dissolving the large molecules to be analyzed in a solvent, then freezing the resultant solution to a temperature which will provide a vapor pressure not greater than approximately $10^{-5}$ torr, and then using a source of energy to desorb large molecules from the surface of the frozen solution while minimizing the risk of fragmentation of the molecules during the desorption step.

It is still another object of this invention to provide a method of preparing samples of one or more large molecules for mass spectral analysis by dissolving the large molecules to be analyzed in a solvent, then freezing the resultant solution, then cooling the frozen solution to a temperature which will provide a vapor pressure not greater than about $10^{-5}$ torr, and then using a source of energy such as laser radiation, ion beam bombardment, or fast atom beam bombardment, to desorb large molecules from the surface of the frozen solution while minimizing the risk of fragmentation of the molecules during the desorption step.

It is a further object of this invention to provide a method of preparing samples of one or more large molecules for mass spectral analysis by dissolving the large molecules to be analyzed in a solvent which will strongly absorb the energy used to desorb the large molecules, then freezing the resultant solution, then cooling the frozen solution to a temperature which will provide a vapor pressure not greater than about $10^{-5}$ torr, and then using a source of energy such as laser radiation, electron beam bombardment, ion beam bombardment, or fast atom beam bombardment, to desorb large molecules from the surface of the frozen solution while minimizing the risk of fragmentation of the molecules during the desorption step.

It is yet a further object of this invention to provide a method of preparing samples of one or more large molecules for mass spectral analysis by dissolving the large molecules to be analyzed in a solvent which will strongly absorb the energy used to desorb the large molecules, then freezing the resultant solution, then cooling the frozen solution to a temperature which will provide a vapor pressure not greater than about $10^{-5}$ torr, then desorbing large molecules from the surface of the frozen sample using a source of energy such as laser radiation, ion beam bombardment, and fast atom beam bombardment, to desorb the large molecules from the frozen solution while minimizing the risk of fragmentation of the molecules during the desorption step, and then exposing the desorbed molecules to a source of ionization energy to ionize the desorbed molecules in preparation for mass spectral analysis of the ionized molecules.

These and other objects of the invention will be apparent from the following description and accompanying drawings.

BRIEF DESCRIPTION OF THE DRAWINGS

FIG. 1 is a flowsheet generally outlining the method of the invention.

FIG. 3 is a fragmentary side section of a portion of FIG. 2 showing a cooling means used to maintain the frozen solution at a sufficiently low temperature to permit desorption of large molecules in a vacuum chamber.

DETAILED DESCRIPTION OF THE INVENTION

Figure 2:
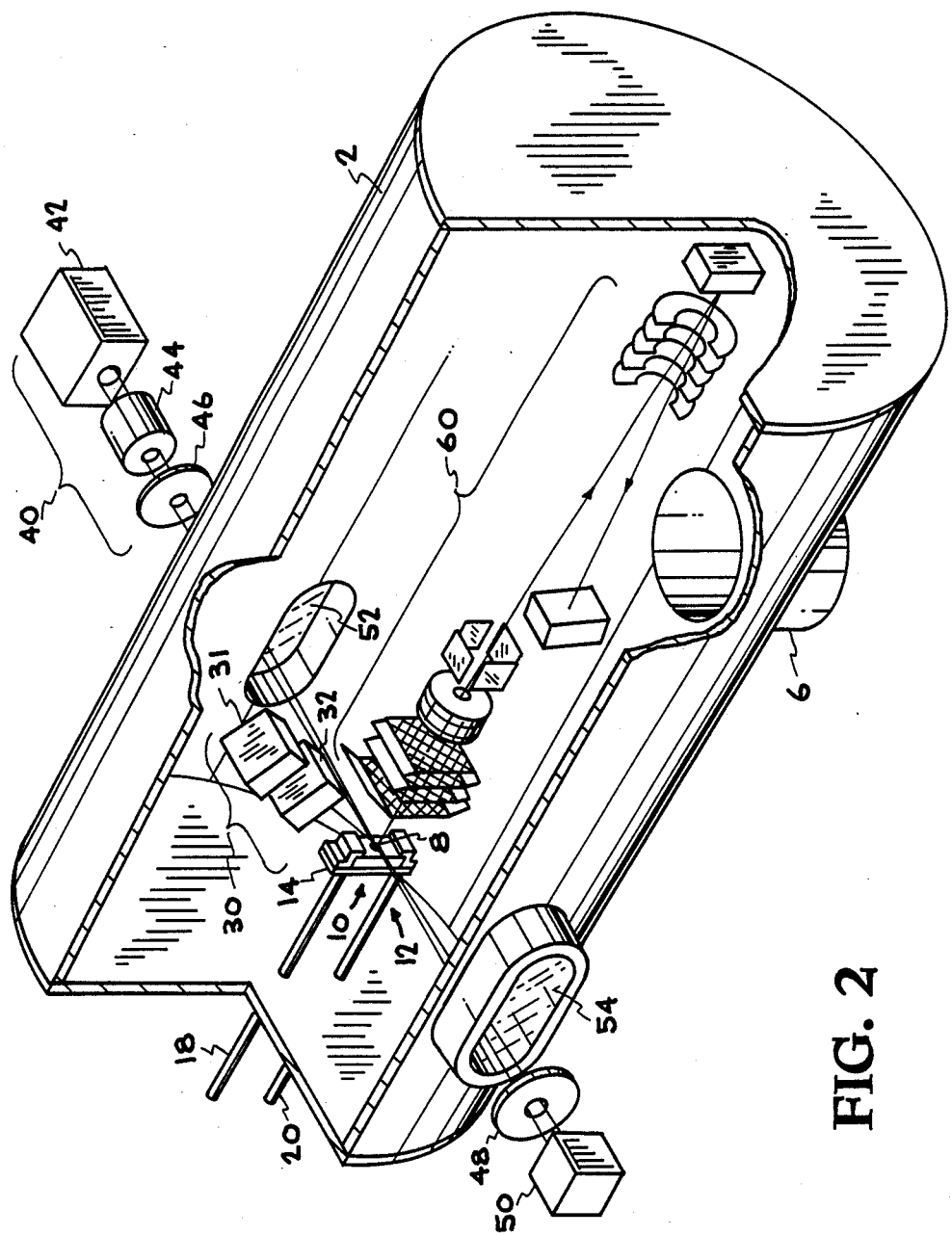
FIG. 2 is a partially cutaway perspective view illustrating apparatus useful in connection with the practice of the method of the invention.

In accordance with the invention, large molecules may be analyzed by mass spectral analysis while minimizing the risk of undesirable fragmentation of the large molecules by first forming a solution of the large molecules in a low molecular weight solvent which is capable of absorbing the energy used to subsequently desorb such large molecules, then freezing the resultant solution, and then exposing the frozen solution to a source of desorbing energy such as a laser, an electron beam, an ion beam, or a source of fast atoms to desorb such large molecules from the surface of the frozen solution.

If the energy source used to desorb the large molecules does not also ionize the molecules, the desorbed molecules may be exposed to a separate source of ionizing energy such as a photoionization source, e.g., a laser beam, to ionize the desorbed molecules prior to analyzing the molecules in a mass spectral analysis apparatus. In either case, fragmentation during the desorption step is either avoided or minimized, so that nonspecific or uncontrolled fragmentation will not occur.

If it is desired to fragment the large molecule or mixture of molecules to provide further means for identification of the molecule(s) through analysis for functional groups by cleavage of the molecule(s) at specified points where such functional groups, if present, would occur, such fragmentation may be done in a separate step where the energy used for such fragmentation can be carefully controlled to avoid nonspecific fragmentation and/or to slowly vary the degree of fragmentation for insight into which functional groups of the molecule were contiguous. Such a subsequent and separate fragmentation step is well known to those skilled in the art and forms no part of this invention.

By forming a frozen solution and then only locally desorbing molecules from the surface of this solution, i.e., preferably desorbing from about 1 to 100 layers of molecules at a time, depending upon the mass of the molecules, i.e., up to about 300 Angstroms depth at a time, it is possible to provide a controlled vaporization of the large molecules while minimizing the exposure of the molecules to large amounts of vaporization energy which could otherwise result in fragmentation or reaction of some of the molecules.

By use of the term "large molecules" is meant a molecule, such as a biomolecule, i.e., a life chemistry molecule, having a molecular weight of at least about five hundred atomic mass units (amu). Examples of the types of large molecules such as biomolecules or life chemistry molecules which may be advantageously processed by the method of this invention while minimizing the risk of fragmentation of such large molecules during the desorption step, include peptides and polysaccharides.

The large molecules are dissolved in a low molecular weight solvent which preferably absorbs strongly energy from the desorption energy source, e.g., strongly absorbs laser light energy at the wavelength of the laser, so that there is little penetration of the desorbing energy into the bulk of the frozen sample to thereby facilitate removal of only the top or top several, i.e., about 1–100, surface layers of molecules from the frozen solution as discussed above.

By "low molecular weight solvent" is meant a solvent comprising one or more compounds consisting essentially of molecules having an atomic weight of less than about 100 amu. Examples of solvents which may be used in the practice of the invention include water, and 1–5 carbon organic solvents such as alcohols, aldehydes, ketones, and organic acids and halogenated derivatives of such organic solvents. The reasons for using such solvents include easy dissolution, entraining the larger solvated molecule in the flow of the more plentiful desorbing solvent molecules, cooling of the internal degrees of freedom of the large molecules by many collisions with the lighter more rapidly moving solvent molecules, rapid energy dissipation during collision sequences, and avoidance of mass interferences due to large differences in mass between solvent and solute molecules.

With respect to degree of absorption by the solvent of energy from the desorption source in accordance with the preferred embodiment, by the term "strongly absorbs" is meant a solvent which will absorb sufficient energy from the desorption source, particularly when the desorption energy source is a laser source, so that about 70 to 100% of the energy is absorbed within about 1 to 10 micrometers of the surface of the frozen solution. This will provide the desired controlled desorption of the large molecules while inhibiting fragmentation of the large molecules during the desorption step, as might more readily occur than if the entire mass of the frozen solution were energized. Unnecessary heating of the sample is, thereby avoided and, by limiting desorption to a very limited range of molecular layers, the desorption can be more controlled and uniform, i.e., independent of the solute molecule(s).

The concentration of the large molecules in the solvent should be sufficiently low so as to avoid significant solute molecule interaction and to allow for the energizing beam - solvent interaction to dominate the overall desorption process so that this process is reliable and uniform, i.e., not strongly dependent on the nature of the solute molecule(s). Therefore, the concentration of the solution should be no more than about one solute molecule per $10^3$ solvent molecules, and typically the concentration will be about one solute molecule or less per $10^4$ solvent molecules.

After forming the solution of large molecules dissolved in the low molecular weight solvent, in accordance with the invention, the solution is frozen to provide a solid material from which the large molecules to be analyzed may be desorbed.

The amount of solution which is frozen to form the sample of frozen solution to be analyzed need not be large, but may comprise as little as one drop, e.g., about 1 microliter as a minimum amount, although larger quantities are permissible.

For the subsequent desorption step itself, it is only necessary that the temperature of the solution be lowered sufficiently to transform the liquid solution into a solid phase. However, the large molecules, after desorption, must be transported into the high vacuum mass spectral analysis apparatus which dictates that the desorption take place in a vacuum chamber.

In view of this, it is necessary that the frozen solution be cooled down, prior to desorption, to a temperature at which the vapor pressure is sufficiently low to permit the frozen solution to be admitted into a vacuum chamber prior to the desorption step. Preferably, the frozen solution should be cooled to a temperature at which the vapor pressure of the frozen solution does not exceed about $10^{-5}$ torr, and preferably does not exceed about $10^{-7}$ torr.

This cooling advantageously may be carried out prior to admitting the frozen solution to the vacuum chamber in which the desorption step will take place. However, it is also within the scope of the invention to further cool down the temperature of the frozen solution after admitting it to the vacuum chamber.

In either event, it is necessary to provide cooling means within the vacuum chamber to maintain the frozen solution at a temperature sufficiently low to maintain the desired low pressure in the vacuum chamber as well as to avoid nonuniform concentration distributions on the top of the sample that would result from preferential solvent evaporation. As will be described below in the description of the apparatus, this may comprise a cold plate in the vacuum chamber on which the frozen solution rests and through which is circulated a coolant from an external cooling source.

Referring now to FIGS. 2 and 3, an apparatus suitably for use in the practice of the invention is generally illustrated. Certain aspects of this apparatus are generally similar to the apparatus illustrated and described with respect to the aforementioned Becker et al U.S. Pat. 4,733,073, cross-reference to which is hereby made for such construction details.

As shown in FIG. 2, a vacuum chamber 2 is provided with a sample holder 10 therein on which is mounted or carried a sample 8 of the frozen solution. Vacuum chamber 2 is further provided with means for evacuation of chamber 2 comprising a port 6 leading to a conventional vacuum pumping means (not shown).

As shown in more detail in FIG. 3, sample holder 10 may further comprise cooling means 12 for maintaining sample 8 at a sufficiently cool temperature to maintain the desired low vapor pressure of at least no more than $10^{-5}$ torr, preferably at least no more than $10^{-7}$ torr.

Cooling means 12 may comprise a metal back plate 14 containing one or more passageways 16 through which coolant may be circulated from an external coolant source 22 via entrance pipe 18 and exit pipe 20.

Desorption energy source means 30, which may be located either internal or external to vacuum chamber 2 (as illustrated) includes desorption energy source 31 and directing means 32. Source 31 may comprise an electron gun, ion gun, or a laser. Neutral atoms or molecules at kilo electron volt energy may also be used as desorption energy source 31. The construction of such energy sources is conventional and is well known to those skilled in the art, for example, from electron beam desorption, ion beam sputtering, or laser microprobe techniques.

Directing means 32, which is coupled to desorption energy source 31 to direct the energy beam from energy source 31 onto sample 8, may comprise electrostatic and/or magnetic focusing and deflection means for charged particle beams or mirrors and lenses for directing and focusing a laser light beam onto the surface of sample 8.

Ionization means 40 are also provided to ionize the desorbed molecules in vacuum chamber 2 for those cases where direct ionization, i.e., ionization during desorption is not suitable. Ionization means 40 may comprises a high intensity light source 42, a focusing lens system 44, and an iris 46 for use in defining the position of the ionizing beam. Ionization beam source 42 will typically be provided by a high-intensity laser or assembly of lasers and optical materials and components coupled together to achieve sufficiently high power for efficient photoionization of the desorbed large molecules to be analyzed.

In the embodiment illustrated in FIG. 2, vacuum chamber 2 may be provided with diametrically opposed windows 52 and 54, through which the ionizing beam of radiation is projected. In this embodiment, ionizing beam source 42 is mounted outside vacuum chamber 2 and the ionizing beam is directed through window 52 to the ionizing region proximate to the surface of sample 8 to be analyzed. The ionization beam continues through window 54, passes through position-defining iris 48, and is received by detector 50, which serves to monitor the light intensity of ionization beam source 42.

Ionization beam source 42 may comprise a laser having a power density in the range of $10^6$ to $10^{12}$ W/cm$^2$ for nonresonant multiphoton ionization. The laser may be pulsed for time-of-flight mass spectrometry with the pulses having a period of about $10^{-8}$ seconds or less. For non-resonant single-photon ionization, less light intensity is needed; generally though, pulses with at least about $10^{11}$ photons per pulse are needed for efficient ionization.

Ionization of the desorbed molecules which do not ionize during desorption may be carried out using single-photon ionization with vacuum ultraviolet (VUV) radiation which is a soft approach for large molecules which is non-selective and can be made quite efficient and therefore sensitive. A coherent beam of light produced nonlinearly, for example, having an energy level of about 10.5 electron volts at 118 nanometers is convenient for a single photon VUV photoionization source. The intensity of the single photon beam source must be controlled so that multiple ionization does not occur. The intensity of the photoionization beam source is, therefore, preferably controlled so that the absorption probability is not more than about 10%.

Multiple photons may also be used to ionize the desorbed molecules if the ionization potential of the particular large molecule to be analyzed is higher than the single photon energy unless shorter wavelengths are used, i.e., wavelengths shorter than about 130 nanometers. However, when multiple photon ionization is used, control of the intensity is particularly important since one may experience runaway absorption conditions in which case uncontrolled fragmentation of the molecule may occur. Generally, laser power densities not exceeding about $10^7$ W/cm$^2$ are appropriate.

It should be noted, however, that whether using single photon or multiple photon ionization, absorption of some additional energy above that needed for ionization by the large molecule to be analyzed may be converted to vibrational energy which may be used to shake off any solvent molecules adhering to the large molecule or the additional absorbed energy may simply be dissipated as kinetic energy in the electron removal.

Vacuum chamber 2 may further include (or be coupled to) mass spectrometer analysis means, indicated generally in FIG. 2 at 60, for mass analysis of the large molecules desorbed and ionized from the frozen solution in accordance with the invention. Alternate forms of mass spectral analysis means 60 are discussed in more detail in the aforementioned and cross-referenced Becker et al U.S. Pat. No. 4,733,073.

Thus, the invention provides a method for processing large molecules for mass spectral analysis in a manner in which desorption from a frozen solution which yields minimal fragmentation or clustering of large molecules during the desorption step. Ionization may be either carried out together with the desorption step or in a separate ionization step, depending upon the molecule(s) being desorbed. Since some characteristic fragmentation is sometimes desirable for mass analysis, the system of the invention lends itself readily to the addition of a purposely fragmenting step (e.g., additional laser radiation or collisional activation) in a controlled fashion. In this way the three processes of desorption, ionization, and, if desired, fragmentation, may be maximally decoupled for the greatest advantage.

Having thus described the invention, what is claimed is:

1. A method useful for preparing a sample of nonvolatile molecules for mass spectral analysis which comprises:
   (a) providing a solution containing one or more types of molecules to be analyzed dissolved in a solvent selected from the class consisting of water, 1–5 carbon organic solvents, and mixtures thereof to form a solution;
   (b) freezing said solution of dissolved molecules to form a frozen solution; and
   (c) exposing said frozen solution to a source of laser radiation energy to desorb molecules to be analyzed from the surface of said frozen solution.

2. The method of claim 1 wherein said step of providing said solution containing one or more molecules to be analyzed dissolved therein further comprises providing a solution having dissolved therein one or more types of molecules having a mass of at least about 500 amu.

3. The method of claim 2 including the further step of transporting the desorbed molecules to a mass spectral analysis zone.

4. The method of claim 2 wherein said step of providing a solution containing said one or more molecules to be analyzed further comprises dissolving said molecules in a solvent which strongly absorbs the energy used to desorb said large molecules to permit desorption of said molecules on the surface of said frozen solution without substantial absorption of said energy below the surface of said frozen solution to thereby inhibit heating of the entire solution.

5. The method of claim 4 wherein said step of dissolving said molecules to be analyzed in a solvent comprises dissolving said molecules in a low molecular weight solvent.

6. The method of claim 5 wherein said step of dissolving said molecules to be analyzed in a low molecular weight solvent further comprises dissolving said molecules in a solvent consisting essentially of solvent molecules having an atomic weight of less than about 100 amu.

7. The method of claim 2 wherein said step of freezing said solution of dissolved molecules further comprises forming a frozen solution having a vapor pressure not greater than $10^{-5}$ torr.

8. The method of claim 2 including the further step of transporting said frozen solution of said molecules to be analyzed to a vacuum chamber and maintaining said frozen solution at a pressure not greater than $10^{-5}$ torr while desorbing said molecules from the surface of said frozen solution.

9. The method of claim 2 wherein said step of exposing said frozen solution of said molecules to be analyzed to a source of energy to desorb said molecules comprises exposing said frozen solution to laser radiation.

10. The method of claim 2 wherein said step of exposing said frozen solution of said molecules to be analyzed to a source of energy to desorb said molecules comprises exposing said frozen solution to ion beam bombardment.

11. The method of claim 2 wherein said step of exposing said frozen solution of said molecules to be analyzed to a source of energy to desorb said molecules comprises exposing said frozen solution to electron beam bombardment.

12. The method of claim 2 wherein said step of exposing said frozen solution of said molecules to be analyzed to a source of energy to desorb said molecules comprises exposing said frozen solution to fast atom beam bombardment.

13. The method of claim 2 wherein said step of exposing said frozen solution to a source of energy to desorb said molecules includes the further step of exposing said desorbed molecules to a source of ionization energy to ionize said desorbed molecules in preparation for mass spectral analysis of said ionized molecules.

14. A method useful for processing large molecules for mass spectral analysis which comprises:
(a) providing a solution containing one or more molecules to be analyzed having a molecular weight of at least about 500 amu dissolved in a low molecular weight solvent capable of absorbing a sufficient amount of the energy subsequently used to desorb said molecules from said solution so that from 70 to 100 % of the energy is absorbed within about 10 micrometers of the surface of the solution when frozen;
(b) freezing said solution of dissolved molecules to form a frozen solution;
(c) maintaining said frozen solution in a vacuum chamber at a temperature sufficiently low to provide a vapor pressure of less than $10^{-5}$ torr;
(d) exposing said frozen solution in said vacuum chamber to a source of laser radiation energy sufficient to desorb from 1 to 100 layers of molecules to be analyzed from the surface of said frozen solution.

15. The method of claim 14 wherein said step of exposing said frozen solution to a source of energy to desorb said molecules does not result in the ionization of such desorbed molecules and said method includes the further step of exposing said desorbed molecules to a source of ionization energy to ionize said desorbed molecules in preparation for mass spectral analysis of said ionized molecules;

16. The method of claim 15 wherein said step of exposing said desorbed molecules to an ionization source to ionize the desorbed molecules further comprises exposing said desorbed molecules to a photoionization source.

17. The method of claim 15 wherein said steps of desorbing said molecules and ionizing said desorbed molecules are carried out in sequential cycles.

18. The method of claim 17 wherein said sequential desorption and ionization steps are carried out by sequentially pulsing said desorption energy source and said ionization source.

19. A method useful for processing large molecules for mass spectral analysis which comprises:
(a) providing a solution containing one or more molecules to be analyzed having a molecular weight of at least about 500 amu dissolved in a low molecular weight solvent to form said solution, said solvent being capable of absorbing a sufficient amount of the energy subsequently used to desorb said molecules from said solution so that from 70 to 100% of the energy is absorbed within about 10 micrometers of the surface of the solution when frozen;
(b) freezing said solution of dissolved molecules to form a frozen solution;
(c) maintaining said frozen solution in a vacuum chamber at a temperature sufficiently low to provide a vapor pressure of less than $10^{-5}$ torr;
(d) exposing said frozen solution in said vacuum chamber to a source of energy sufficient to desorb from 1 to 100 layers of molecules to be analyzed from the surface of said frozen solution and selected from the class consisting of laser radiation, ion beam bombardment, electron beam bombardment, and fast atom beam bombardment.

20. The method of claim 19 including the further step of exposing said desorbed molecules to an ionization source of sufficient intensity to ionize said desorbed molecules.

21. The method of claim 19 wherein said step of maintaining said frozen solution in a vacuum chamber at a temperature sufficiently low to provide a vapor pressure of less than $10^{-5}$ torr includes the further steps of first cooling said frozen solution down to said temperature and then introducing said cooled frozen solution into said vacuum chamber.

22. The method of claim 19 wherein said step of maintaining said frozen solution in a vacuum chamber at a temperature sufficiently low to provide a vapor pressure of less than $10^{-5}$ torr includes the further steps of first introducing said cooled frozen solution into said vacuum chamber and then cooling said frozen solution down to said temperature.

23. A method useful for preparing a sample of non-volatile molecules for mass spectral analysis which comprises:
(a) providing a solution comprising one or more types of molecules having a mass of at least about 500 AMU to be analyzed dissolved in a low molecular weight solvent selected from the class consisting of water, 1-5 carbon organic solvents, and mixtures thereof, which solvent strongly absorbs the energy used to desorb said large molecules to permit desorption of said molecules on the surface of a frozen solution without substantial absorption of said energy below the surface of said frozen solution to thereby inhibit heating of the entire solution;
(b) freezing said solution of dissolved molecules to form a frozen solution; and
(c) exposing said frozen solution to a source of laser radiation energy to desorb molecules to be analyzed from the surface of said frozen solution.

24. A method useful for preparing a sample of thermally labile molecules for mass spectral analysis while minimizing the risk of fragmentation of such molecules during desorption which comprises:
(a) forming a solution by dissolving one or more types of such thermally labile molecules to be analyzed in a solvent capable of absorbing from 70 to 100% of the energy from a desorbing energy source within about 10 micrometers of the surface of the solution when frozen;
(b) freezing said solution of dissolved molecules to form a frozen solution; and
(c) exposing said frozen solution to a source of laser radiation energy to desorb molecules to be analyzed from the surface of said frozen solution.

* * * * *